US007811318B2

(12) United States Patent
Yavorski et al.

(10) Patent No.: US 7,811,318 B2
(45) Date of Patent: Oct. 12, 2010

(54) APPARATUS AND METHOD FOR PNEUMATICALLY DRIVING AN IMPLANTABLE MEDICAL DEVICE

(75) Inventors: David Yavorski, Tucson, AZ (US); Leonard M. Faria, Bristol, RI (US); James W. Kelland, E. Walpole, MA (US); Douglas M. Riker, W. Roxbury, MA (US)

(73) Assignee: SynCardia Systems, Inc., Tucson, AZ (US)

( * ) Notice: Subject to any disclaimer, the term of this patent is extended or adjusted under 35 U.S.C. 154(b) by 142 days.

(21) Appl. No.: 12/108,436

(22) Filed: Apr. 23, 2008

(65) Prior Publication Data
US 2009/0270981 A1  Oct. 29, 2009

(51) Int. Cl.
*A61M 1/10* (2006.01)
(52) U.S. Cl. .................. 623/3.1; 417/395; 91/510
(58) Field of Classification Search .............. 623/3.1, 623/3.16, 3.27, 3.28; 600/16, 300; 417/395; 91/510, 536, 171
See application file for complete search history.

(56) References Cited

U.S. PATENT DOCUMENTS

| 3,585,902 | A | * | 6/1971 | Anderson ............ 91/363 A |
| 3,587,567 | A | | 6/1971 | Schiff |
| 3,590,815 | A | | 7/1971 | Schiff |
| 3,641,591 | A | | 2/1972 | Kolff |
| 3,985,123 | A | | 10/1976 | Herzlinger et al. |
| 4,222,127 | A | | 9/1980 | Donachy et al. |
| 4,427,470 | A | | 1/1984 | Kolff |
| 4,573,997 | A | | 3/1986 | Wisman et al. |
| 4,611,578 | A | | 9/1986 | Heimes |
| 4,650,485 | A | | 3/1987 | Della Sala |
| 4,662,358 | A | | 5/1987 | Farrar et al. |
| 4,782,817 | A | | 11/1988 | Singh et al. |
| 4,808,088 | A | | 2/1989 | Missfeldt |
| 4,813,952 | A | * | 3/1989 | Khalafalla .............. 600/17 |
| 4,825,748 | A | * | 5/1989 | Sheng ................. 91/171 |
| 4,863,461 | A | | 9/1989 | Jarvik |
| 4,902,291 | A | | 2/1990 | Kolff |
| 4,957,107 | A | | 9/1990 | Sipin |
| 5,282,849 | A | | 2/1994 | Kolff et al. |
| 5,632,623 | A | | 5/1997 | Kolff et al. |
| 5,738,627 | A | | 4/1998 | Kovacs et al. |
| 5,749,839 | A | | 5/1998 | Kovacs |

(Continued)

OTHER PUBLICATIONS

Website: http://www.syncardia.com/formedical/index.php "CardioWest temporary Total Artificial Heart" 2007.

(Continued)

*Primary Examiner*—Corrine M McDermott
*Assistant Examiner*—Matthew Schall
(74) *Attorney, Agent, or Firm*—Wolf, Greenfield & Sacks, P.C.

(57) ABSTRACT

A driver is disclosed for powering a pneumatically operated implantable device, such as an artificial heart with a left and a right ventricle. The driver includes a pair of compressors that each has a first and a second compression chamber. In a first mode of operation, both the first and the second compressor power the left and right ventricle of the artificial heart. In the event of a malfunction in the second compressor, the left and right ventricles of the artificial heart may be powered by the first compressor. Similarly, if a malfunction occurs in the first compressor, the artificial heart may be fully powered by the second compressor.

14 Claims, 7 Drawing Sheets

U.S. PATENT DOCUMENTS

| | | | |
|---|---|---|---|
| 5,759,148 | A | 6/1998 | Sipin |
| 5,766,207 | A * | 6/1998 | Potter et al. .................. 600/16 |
| 6,123,726 | A | 9/2000 | Mori et al. |
| 6,511,413 | B2 | 1/2003 | Landesberg |
| 7,074,176 | B2 | 7/2006 | Sacristan |
| 2005/0027173 | A1 * | 2/2005 | Briscoe et al. ............. 600/300 |
| 2007/0084206 | A1 * | 4/2007 | Lew et al. .................... 60/599 |
| 2008/0064917 | A1 * | 3/2008 | Bar et al. ...................... 600/16 |

OTHER PUBLICATIONS

Thoratec® TLC-II® Portable Pneumatic Driver Instructions for Use; Thoratec Coporation, "Thoratec® TLC-II® Portable VAD Driver and System" pp. 1-95, 2005.

SynCardia Systems, Inc. EXCOR TAH-t Operator Manual REV. 004, E-1000049, "EXCOR-TAH-t System for the CardioWest™ TAH-t" pp. 1-119, 2007.

* cited by examiner

US 7,811,318 B2

APPARATUS AND METHOD FOR PNEUMATICALLY DRIVING AN IMPLANTABLE MEDICAL DEVICE

BACKGROUND

1. Field

The present invention relates to apparatus and methods for driving a pneumatically operated implantable device, such as an artificial heart.

2. Discussion of Related Art

Artificial hearts are typically constructed with right and left ventricles that function generally like and may replace the right and left ventricles of a native heart. The right ventricle receives oxygen-poor blood from the subject's body and delivers this blood to the lungs for oxygenation. The left ventricle receives oxygen-rich blood from the lungs of a subject and delivers this blood throughout the subject's body.

Each ventricle of the artificial heart 100, like that shown in FIG. 1, includes a movable diaphragm 102 that is positioned between an air chamber 104 and a blood chamber 106 within the ventricle. The air chamber includes a single inlet/outlet 108 that is in fluid communication with a pneumatic driver. A blood inlet valve 110 provides a one-way entrance into the blood chamber 106 from the circulatory system of a subject and a blood outlet valve 112 provides a one-way outlet from the blood chamber.

To replicate the systole of a native heart, pressurized air is provided to the air chamber in each ventricle of the artificial heart. The pressurized air displaces the diaphragm within the ventricle, reducing the volume of the blood chamber and causing blood to be ejected through the outlet valve and into the circulatory system of the subject. To replicate the diastole of a native heart, pressure is relieved from the air chamber of the ventricle, which allows blood to enter the blood chamber from the circulatory system of the subject.

One example of an artificial heart is the CARDIOWEST Total Artificial Heart (TAH-t), as illustrated in FIG. 1. The TAH-t has left 114 and right 116 ventricles with a displacement of 70 cubic centimeters each. The TAH-t is used as a bridge-to-transplant type device, whereby the TAH-t is configured to replace a diseased heart on a temporary basis until a subject receives a transplanted human heart. The TAH-t may potentially, however, also be used as a permanent replacement for a native heart.

SUMMARY

According to one aspect, a pulsatile pneumatic driver is configured to provide pneumatic power to an implantable artificial heart. The driver includes a first compressor that includes a first pair of compression chambers and at least one of the first pair of compression chambers has a swept volume that is greater than about 160 cubic centimeters. The driver also includes a second compressor that includes a second pair of compression chambers, where at least one of the second pair of compression chambers has a swept volume that is greater than about 160 cubic centimeters. A first air outlet and a second air outlet are in selective communication with two or more compression chambers of the first and second pair of compression chambers. A valve is movable between a normal operation position associated with a normal mode of operation of the driver, a first backup position associated with a first backup mode of operation of the driver and a second backup position associated with a second backup mode of operation of the driver. When in the normal mode of operation, the first air outlet is in fluid communication with one of the first pair of compression chambers and the second air outlet is in fluid communication with one of the second pair of compression chambers. When in the first backup mode of operation, the first air outlet is in fluid communication with one of the first pair of compression chambers and the second air outlet is in fluid communication with another of the first pair of compression chambers. When in the second backup mode of operation, the first air outlet is in fluid communication with one of the second pair of compression chambers and the second air outlet is in fluid communication with another of the second pair of compression chambers.

According to another aspect, a pulsatile pneumatic driver is configured to provide pneumatic power to an implantable artificial heart. The driver comprises a first compressor that includes a first pair of compression chambers and a second compressor that includes a second pair of compression chambers. A first air outlet and a second air outlet are each in selective communication with two or more compression chambers of the first and second pair of compression chambers. A valve is movable between a normal operation position associated with a normal mode of operation of the driver, a first backup position associated with a first backup mode of operation of the driver and a second backup position associated with a second backup mode of operation of the driver. When in the normal mode of operation, the first air outlet is in fluid communication with one of the first pair of compression chambers and the second air outlet is in fluid communication with one of the second pair of compression chambers. When in the first backup mode of operation, the first air outlet is in fluid communication with one of the first pair of compression chambers and the second air outlet is in fluid communication with another of the first pair of compression chambers. When in the second backup mode of operation, the first air outlet is in fluid communication with one of the second pair of compression chambers and the second air outlet is in fluid communication with another of the second pair of compression chambers. The driver also comprises a controller that monitors operation of the driver and upon detection of a fault causes the valve to move from the normal operation position to one of the first and second backup positions. The fault comprises the first and second compressors operating more than 180 degrees out of phase with one another.

According to another aspect, a pulsatile pneumatic driver is configured to provide pneumatic power to an implantable artificial heart. The driver comprises a first compressor that includes a first pair of compression chambers and a second compressor that includes a second pair of compression chambers. A first air outlet and a second air outlet are each in selective communication with two or more compression chambers of the first and second pair of compression chambers. A valve is movable between a normal operation position associated with a normal mode of operation of the driver, a first backup position associated with a first backup mode of operation of the driver and a second backup position associated with a second backup mode of operation of the driver. When in the normal mode of operation, the first air outlet is in fluid communication with one of the first pair of compression chambers and the second air outlet is in fluid communication with one of the second pair of compression chambers. When in the first backup mode of operation, the first air outlet is in fluid communication with one of the first pair of compression chambers and the second air outlet is in fluid communication with another of the first pair of compression chambers. When in the second backup mode of operation, the first air outlet is in fluid communication with one of the second pair of compression chambers and the second air outlet is in fluid communication with another of the second pair of compression chambers upon detection of a fault. The driver also comprises a controller that monitors operation of the driver and causes the valve to move the normal operation position to one of the first and second backup positions. The controller monitors a first pair of redundant position sensors associated with the first compressor and a second pair of redundant position sensors associated with the second compressor to determine the fault.

According to another aspect, a pulsatile pneumatic driver is configured to provide pneumatic power to an implantable artificial heart. The driver comprises a first compressor that includes a first pair of compression chambers and a second compressor that includes a second pair of compression chambers. A first air outlet and a second air outlet are each in selective communication with two or more compression chambers of the first and second pair of compression chambers. A valve is movable between a normal operation position associated with a normal mode of operation of the driver, a first backup position associated with a first backup mode of operation of the driver and a second backup position associated with a second backup mode of operation of the driver. When in the normal mode of operation, the first air outlet is in fluid communication with one of the first pair of compression chambers and the second air outlet is in fluid communication with one of the second pair of compression chambers. When in the first backup mode of operation, the first air outlet is in fluid communication with one of the first pair of compression chambers and the second air outlet is in fluid communication with another of the first pair of compression chambers. When in the second backup mode of operation, the first air outlet is in fluid communication with one of the second pair of compression chambers and the second air outlet is in fluid communication with another of the second pair of compression chambers. The driver also comprises a controller that monitors operation of the driver and moves the valve from the normal operation position to one of the first and second backup positions, upon detection of a fault. The controller monitors a pressure and flow rate associated with each of the first and second air outlets to identify the fault.

According to another aspect, a pulsatile pneumatic driver is configured to provide pneumatic power to an implantable artificial heart. The driver comprises a first compressor that includes a first pair of compression chamber and a second compressor that includes a second pair of compression chambers. A first air outlet and a second air outlet are each in selective communication with two or more compression chambers of the first and second pair of compression chambers. A valve is movable between a normal operation position associated with a normal mode of operation of the driver, a first backup position associated with a first backup mode of operation of the driver and a second backup position associated with a second backup mode of operation of the driver. When in the normal mode of operation, the first air outlet is in fluid communication with one of the first pair of compression chambers and the second air outlet is in fluid communication with one of the second pair of compression chambers. When in the first backup mode of operation, the first air outlet is in fluid communication with one of the first pair of compression chambers and the second air outlet is in fluid communication with another of the first pair of compression chambers. When in the second backup mode of operation, the first air outlet is in fluid communication with one of the second pair of compression chambers and the second air outlet is in fluid communication with another of the second pair of compression chambers. A computer is incorporated into the driver that is loaded with software capable of controlling the driver between the normal mode of operation and the first and second backup mode of operation. An analog controller is also incorporated into the driver and includes firmware capable of controlling the driver between the normal mode of operation and the first and second backup modes of operation, independent of the computer.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

Various embodiments of the invention will now be described, by way of example, with reference to the accompanying drawings, in which.

DETAILED DESCRIPTION

Figure 1:
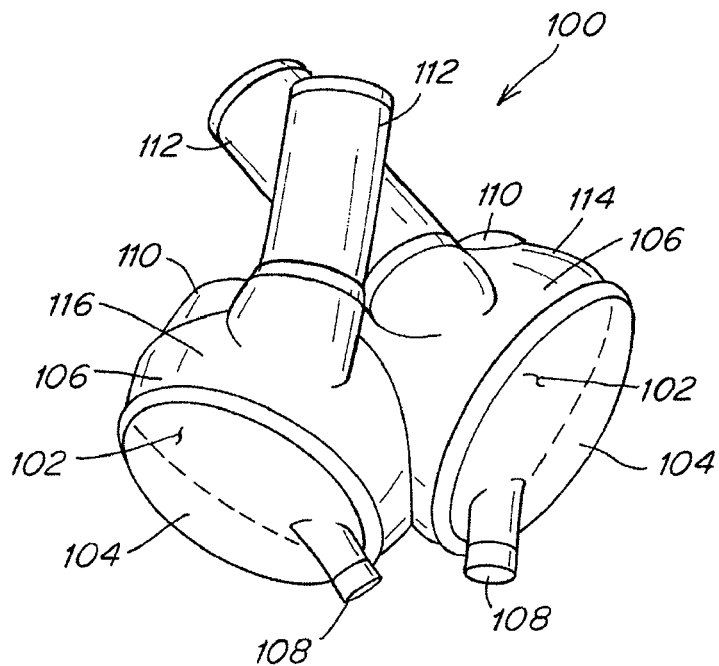
FIG. 1 shows the CARDIOWEST total artificial heart.

Systems described herein relate to a driver that provides pulsatile pneumatic power to an implantable, pneumatically driven medical device, such as an artificial heart. The implantable device may replace or assist the action of a native heart in pumping blood through the circulatory system of a subject.

The driver, according to some embodiments, includes various redundant systems such that the driver may still power an implantable device in the event of fault. By way of example, the driver, in some embodiments, includes a pair of compressors each of which has two compression chambers and a valve that fluidly couples the compressors to an implantable device. In a primary or normal mode of operation, left and right ventricles of an artificial heart are powered by separate compressors in the driver. In the event of a fault in one of the pair of compressors, the valve may be actuated such that both the left and right ventricles are powered by the other of the compressors in a backup mode.

A controller of the driver, according to some embodiments, may be configured to monitor operation of the driver and automatically switch the driver to backup mode from primary mode upon identifying one of several faults. One fault may be identified when the compressors in the driver are operating out of phase with one another, beyond a predetermined threshold, such as 180 degrees. Another fault may include a condition where motion of a piston or other component of either compressor stops for a period of time, or slows below a threshold value. Other faults may include conditions where combinations of pressure and flow exceed or fall below predetermined threshold levels.

Compressors of the driver may be configured to provide pneumatic power to different types of implantable medical devices that are used to assist or replace the function of a native heart. As is to be appreciated, different implantable devices may require varying pressure and flow characteristics to properly assist or replace the function of the native heart. The driver, according to some embodiments, includes features that allow the compressors to be driven at different rates and according to different velocity profiles to accommodate the functional needs of different devices.

Embodiments of the driver may additionally or alternately include redundant power sources and/or redundant control systems. By way of example, some embodiments include one or more rechargeable internal batteries and/or one or more rechargeable external batteries. Additionally or alternatively, some embodiments include an onboard computer that includes software capable of operating the driver in addition to printed circuit board based firmware that may control the driver, in the event of fault with the computer or associated software.

The driver may include compressors sized to provide pulsatile pneumatic power to implantable devices with relatively high power requirements, including artificial hearts that replace the function of a native heart, and may do so over a complete range of operating conditions. Embodiments of the driver may be capable of powering such devices through their complete range of operating condition at high altitudes, such as 8000' feet above sea level or higher, where ambient air is less dense. Additionally or alternatively, embodiments of the driver may provide a complete range of power even when connected to an implantable device through drivelines that include a relatively large dead volume. In this respect, embodiments of the driver may be suitable for use in an operating room setting, where longer drivelines (up to 7 feet or greater) with relatively large dead volumes may be used to connect the driver and implantable device.

Compressors in various embodiments of the driver may be configured to power implantable devices with pulsatile pneumatic power in a highly responsive manner. That is, the motion a compression chamber of the driver may cause blood to be pumped by an artificial heart with little lag time. This may be accomplished, according to some embodiments, by sizing the compression chambers to have a large swept volume, at least when compared to the displacement of the artificial heart and/or any dead volume in the system.

The driver, according to some embodiments, may be configured for extended maintenance intervals. This may be accomplished, according to some embodiments, by using seals that do not require lubrication, such as glass impregnated TEFLON seals.

The driver may include multiple modes of operation suitable for different settings and/or different users. An operating room mode may allow full access and control by a user, such as a surgeon or surgeon's assistant, to a wide variety of operating parameters including heart rate, flow, peak pressure, and/or pressure waveforms, to name a few. Changes to these parameters may be made immediately after desired levels are input to the controller. In an intensive care mode, there may be more limited access to the number of parameters that may be changed and/or to the degree which such parameters may be changed. Additionally, the driver may pause and/or request confirmation before changes to such parameters are implemented. In a home mode, parameters may be locked, such that they may not be changed by a user or may only be changed to a limited degree. The ability to change between modes may require a password or other security feature, according to some embodiments.

The driver may monitor and/or record various operating parameters of the subject and/or driver, such as heart rate, pressure waveforms, peak pressures, flow rates, cardiac output, and the like. According to some embodiments, the driver includes a graphical user interface for the display of such parameters. The controller and graphical user interface may also provide for the review of previously recorded parameters.

Embodiments of the driver may be readily dockable to different host devices. In on embodiment, the host device may be a hospital cart that includes additional user interfaces and that may be suitable for use in and movement about a hospital setting. The driver may also be dockable to a personal caddy that helps a subject to be mobile with the driver outside of a hospital setting. Electrical and mechanical connections between the driver and a dock on the cart or caddy may be automatically engaged to facilitate an easy connection.

For ease of understanding, the pneumatic driver will be described herein in connection with a system that includes an artificial heart. It is to be appreciated, however, that the driver may also be used to provide pneumatic power to other types of implantable devices, such as ventricular assist devices, intra-aortic balloon pumps, and the like.

Figure 2:
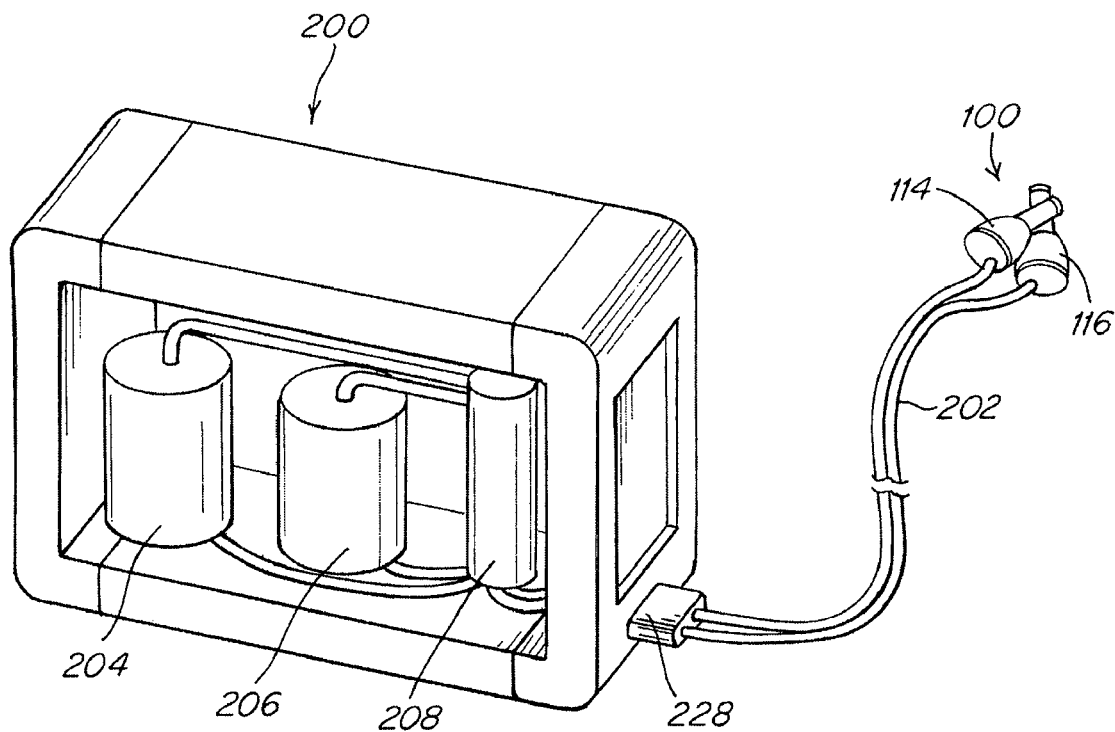
FIG. 2 shows a perspective view of a driver and an artificial heart, connected to the driver, according to one embodiment.

As shown in FIG. 2, embodiments of the system may include an artificial heart 100 with a left ventricle 114 and right 116 ventricle, a driver 200, and pair of drivelines 202 that pneumatically connect each ventricle of the artificial heart 100 to the driver. The driver 200 includes compression chambers that expand and contract to cause air chambers in the ventricles of the artificial heart to contract and expand, respectively. This contraction and expansion of the ventricles may cause blood to be pumped through the circulatory system of a subject.

As shown in FIG. 2, the driver may include a first compressor 204 and a second compressor 206. Each compressor has a first and a second compression chamber, such that the driver includes four compression chambers that may be used to drive the left and right ventricles of the artificial heart 100. The driver may also include one or more valves 208 that selectively connect the left and right ventricles of the artificial heart to different compression chambers in the driver, according to different modes of operation.

Figure 3:
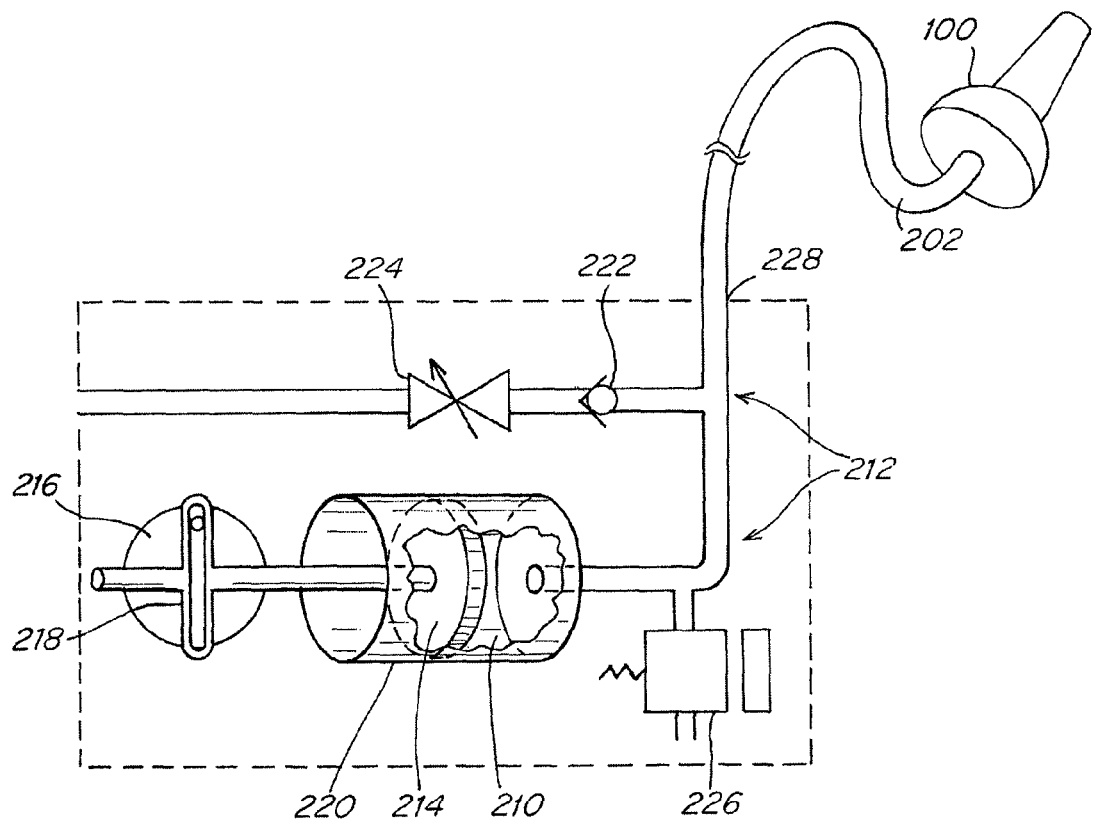
FIG. 3 shows a schematic view of a single compression chamber and other portions of a pneumatic system that may be incorporated into a driver used to drive an implantable device, according to one embodiment.

FIG. 3 is a schematic view of a pneumatic system 212 that includes a single compression chamber 210 that may be incorporated into a driver used to drive one chamber (e.g., one ventricle) of an implantable device. The compression chamber includes a piston 214 that is moved by a motor 216 through a cylinder 220 from a bottom dead center position to a top dead center position and then back to the bottom dead center position. The swept volume of the compression chamber is defined by the volume displaced by the piston 214 when moved from the bottom to top dead center position. In addition to the compression chamber, the pneumatic system also comprises a check valve 222, a vacuum valve 224, a pressure relief valve 226, an air outlet 228 and plumbing to fluidly connect each of these components, as described in greater detail herein. A tube-like driveline 202 may connect the air outlet of the driver to the air chamber of an implantable device. Pressure sensors and air flow meters are also incorporated into the pneumatic system.

In the embodiment of FIG. 3, compression begins as the piston moves away from the bottom dead center position. This movement compresses air in the compression chamber 210 and other portions of the pneumatic system 212. This compression, in turn, causes expansion of the air chamber 104 in a corresponding ventricle of the artificial heart 100, moving the diaphragm 102 toward the blood chamber 106 to eject blood to the circulatory system of the subject. The piston 214 then returns to the bottom dead center position. Blood flows into the blood chamber 106 through the inlet valve 110. The cycle is then repeated with movement of the piston away from the bottom dead center position.

Blood filling of the chamber may occur with different degrees of vacuum assist or with no vacuum assist at all. According to some embodiments, the vacuum valve 224 is closed completely, such that no ambient air enters the pneumatic system 212 as the compression chamber expands. In this mode of operation, the air chamber of the artificial heart is compressed relatively quickly by movement of the piston toward bottom dead center, causing blood to be pulled into the blood chamber more rapidly. In other modes of operation, the pneumatic system 212 may be opened to atmospheric pressure through the vacuum valve 224 as the compression chamber expands. This allows atmospheric air to enter the pneumatic system 212 thus reducing the level of vacuum that is applied to the air chamber 104 of the artificial heart, and slowing the rate at which blood flows into the blood chamber 106. In some embodiments, the vacuum valve may be opened wide enough such that no vacuum is applied to the air chamber of the artificial heart. Here, blood filling may occur solely as a result of residual blood pressure in the circulatory system expanding the blood chamber.

Figure 4:
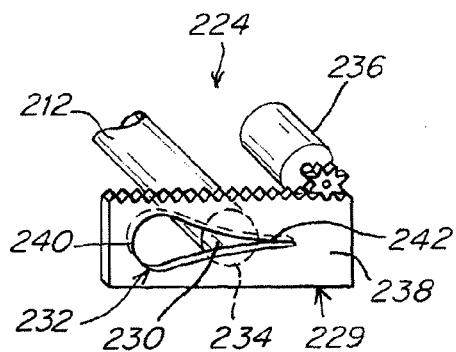
FIG. 4 shows a vacuum valve that includes a variably adjustable aperture, according to one embodiment.

According to some embodiments, the vacuum valve 224 may include a variably adjustable aperture. In this respect, the level of vacuum and thus the rate at which blood flows into the blood chamber of a ventricle may be selectively controlled. As shown in FIG. 4, the vacuum valve 224 may have features that allow precise adjustment of the aperture size and thus high resolution adjustment of the vacuum level during blood filling. According to some embodiments, the aperture 230 may be sized such that the vacuum level may be controlled in increments of 1 mmHg or less.

In the embodiment of FIG. 4, the vacuum valve is configured as a sliding gate valve 229 with a tear-drop shaped aperture 232 that may be moved relative to a stationary, circular aperture 234. A stepper motor 236 moves the gate valve from a fully closed position, where a solid portion 238 of the gate blocks the stationary aperture, to a fully open position, where the circular portion 240 of the tear-drop shaped aperture is aligned with the stationary aperture 234. The tail portion 242 of the tear-drop shaped aperture, when moved across the stationary aperture 234, makes minor incremental adjustments to the cross-sectional area of the vacuum valve aperture, which allows the vacuum level to be tuned more finely than would be capable with only the stepper motor and apertures having other geometries. It is to be appreciated that the tear-drop shaped valve is but one shape that may be incorporated into a sliding gate of a valve, and that other shapes, such as triangles, and the like, may also be used to provide a finely tunable vacuum valve. Additionally, variable adjustable apertures may be incorporated into other types of valves, as this concept is not limited to gate valves.

The level of vacuum may be controlled based on different input criteria. According to some embodiments, the vacuum valve aperture is adjusted based on the heart rate and/or peak blood pressure of a subject. According to other embodiments, the vacuum valve controls the level of vacuum during blood filling to a constant level, regardless of the heart rate and/or blood pressure. Typically, the pressure in the air chamber is controlled to a value that lies between 0 mmHg and −30 mmHg, although other vacuum values are also possible.

Fluidic access to the vacuum valve 224 may be closed to prevent the escape of air as the compression chamber 210 contracts. In the embodiment of FIG. 3, this is accomplished by a check valve 222 that closes shortly after the pressure level in the pneumatic system 212 begins to rise. The check valve 222 isolates the vacuum valve 224 from remaining portions of the pneumatic system 212, such that pressure is directed solely to the air outlet 228 and any associated implantable device 100, rather than out of the driver through the vacuum valve 224. According to some embodiments, the check valve includes one or more leaflets that are positioned against an aperture of the vacuum valve. Leaflet valves may prove prevent portions of the check valve from entering the aperture of the vacuum valve. In one embodiment, the check valve is a bi-leaflet check valve.

A pressure relief valve 226, as shown in FIG. 3, may be included in the pneumatic system 212 to prevent air pressure from exceeding a set pressure value. According to some embodiments, the pressure relief 226 valve is configured to define the peak pressure experienced during systole by releasing air once the peak pressure is achieved by a compressor. In these embodiments, the pressure relief valve will typically open at some point during every compression cycle. In other embodiments, peak pressure may primarily be controlled by the compression chamber that is driving an artificial heart, such that the pressure relief valve acts more as a safety valve that prevents over-pressurization of the air chamber in an artificial heart. In such embodiments, the pressure relief valve may not typically open during every cycle.

The pressure relief valve 226 and/or the vacuum valve 224 may also include features to help maintain a target set point. In one embodiment, a pressure sensor measures the air pressure in the pneumatic system 212 of the driver. A controller that is incorporated into the driver uses readings from the pressure sensor to decide when to activate the pressure relief valve 226 and/or the vacuum valve 224 and/or how far to open such valves. The controller may incorporate various types of control schemes, including but not limited to Proportional control (P control), Proportional-Integral control (PI control), and/or Proportional-Integral-Derivative control (PID control). Use of such control schemes may help accommodate wear that occurs in the pressure valve, and that might otherwise cause a set point of the pressure valve to drift.

Embodiments of the pressure relief valve 226 may, additionally or alternately, be controlled to open at a set pressure that is independent on other operating parameters of the driver and/or physiological conditions of a subject. By way of example, the set point may increase to a higher pressure when the subject is sensed to be active, thus requiring greater pressures to pump an equivalent amount of blood flow through the circulatory system of the subject. Set points may also vary for different types of implantable devices, or among the left and right ventricles of an artificial heart. By way of example, the right ventricle of an artificial heart (or a native heart) is typically associated with a lower peak pressure than the left ventricle. According to some embodiments of the driver configured for use with the CARDIOWEST TAH-t, pressure relieve valves may be set to maintain a peak right ventricle pressure of between 40 mmHg and 150 mmHg, and a left ventricle peak pressure of between 120 mmHg and 280 mmHg.

The pneumatic system 212 may be configured such that an implantable device responds rapidly to compression of the compression chamber. According to some embodiments, this may be accomplished by having compression chambers with swept volumes that are relatively large when compared to the displacement of a corresponding implantable device and/or dead volume of the pneumatic system. The volume of the pneumatic system comprises the swept volume of the compression chamber, the displacement of an associated implantable device, and dead volume that includes the remaining volume of tubes, valves, and the like that fluidly connect the compression chamber to the implantable device when air is being compressed. Reducing the dead volume reduces the total volume of air that is compressed as the compression chamber contracts, and thus may allow a quicker reaction to occur in an implantable device. Similarly, increasing the swept volume of the compression chamber relative to the displacement of an implantable device may also allow for a quicker reaction in an implantable device.

According to one embodiment, the swept volume of the compression chambers in the compressor(s) is at least about 160 cubic centimeters. However, in other embodiments, the swept volume may be 180 cubic centimeters or more, 200 cubic centimeters or more, 225 cubic centimeters or more, 250 cubic centimeters or more, or even greater than 300 cubic centimeters. Displacement of the right ventricle of the artificial heart may be 70 cubic centimeters, according to one embodiment, and the dead volume of the system may be approximately 85 cubic centimeters. The ratio of compression chamber swept volume to implantable device displacement may range from about 2.3 to about 4.3, according to some embodiments, although other values are also possible. The ratio of the swept volume of the compression chamber to the sum of the implantable device displacement and dead volume may range from about 1.0 to about 2.0, according to some embodiments, although ratios outside of this range are also possible. It is to be appreciated that other volumes of compression chamber swept volumes, implantable device displacements, and dead volumes are also possible, and that the above described embodiments are merely exemplary.

Sizing the compressor to have a relatively large swept volume, when compared to the dead volume and/or displacement of an implantable device, may also help the compressor achieve desired peak pressures across a broad range of operating conditions. According to some embodiments, peak pressures of up to about 300 mmHg may be obtained in the left ventricle and peak pressures of up to about 150 mmHg may be obtained in a right ventricle of an artificial heart. These pressures may be achieved across a complete range of heart rates, which in some embodiments, extend from 40 beats per minute (bpm) to 150 bpm. It is to be appreciated, however, that embodiments may be configured to obtain other peak pressure values, lower or higher than these, as these values are merely examples associated with some embodiments.

Sizing compressors to have swept volumes as described above may allow for greater dead space in the pneumatic system, such as might be associated with relatively long drivelines. Drivelines of up to 7 feet and greater, may prove particularly useful in an operating room setting, where it may be desirable to position the driver away from the subject to provide access to the subject for surgeons and other healthcare professionals. Swept volumes sized in this manner may also facilitate driving an artificial heart at higher altitudes, such as those at 8000 feet or higher above sea level.

The compression chamber may be configured to contract and/or expand at different rates to accomplish various effects in an implantable medical device. In one illustrative embodiment shown in FIG. 5, a double peaked pressure waveform 300 of the air chamber 104 in an artificial heart 100 is shown during systole. The initial 302 and secondary 304 pressure peaks, as shown, may help signal proper blood ejection from an artificial heart 100, according to some embodiments. Initially, the waveform of FIG. 5, the diaphragm 102 is positioned such that the volume of the air chamber 104 is minimized and the volume of the blood chamber 106 is maximized. At the beginning of systole, air enters the air chamber without moving the diaphragm. Pressure increases initially until a first peak 302 is reached. At the first pressure peak 302 the diaphragm 102 begins to move, which causes the inlet valve 110 of the blood chamber to close and the outlet valve 112 from the blood chamber to open. Movement of the diaphragm 102 is associated with a slight drop in pressure, and a short, relatively constant pressure level 306 as the diaphragm moves through its full range of motion and blood is ejected through the outlet valve 112. Pressure increases sharply to a second pressure peak 304 as the diaphragm is fully extended into the blood chamber and the volume of the air chamber can no longer be increased. The second peak pressure 304 may be associated with opening of the relieve valve, according to some embodiments. It is to be appreciated that FIG. 5 represents but one type of air chamber pressure waveform that may prove desirable under certain circumstances, and that other pressure waveforms may also offer certain advantages.

Figure 5:
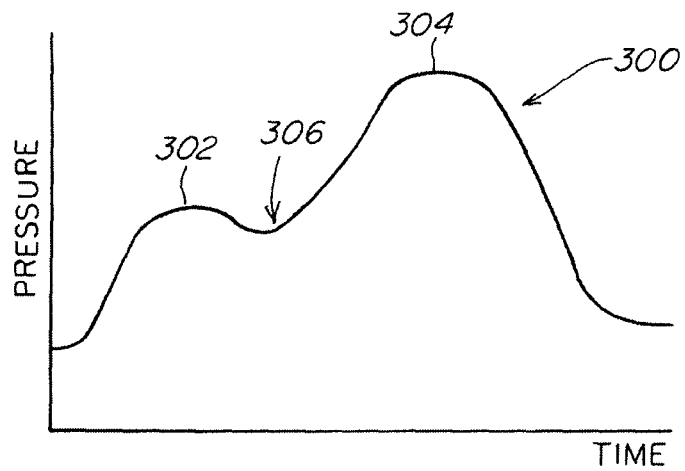
FIG. 5 shows a waveform representative of pressure in the air chamber of an artificial heart, according to one embodiment.
Figure 6:
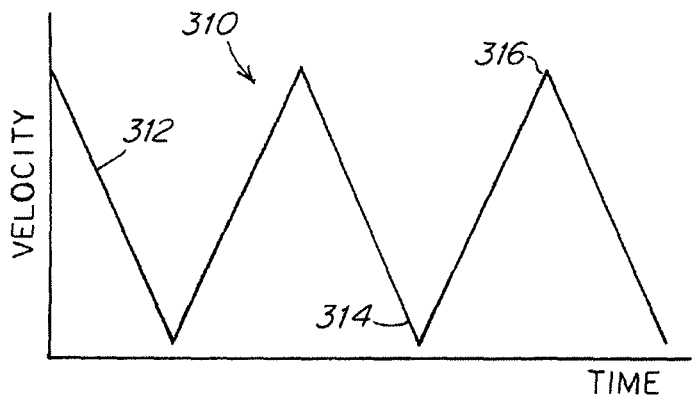
FIG. 6 shows a double saw tooth velocity profile of a piston moving through a compression chamber, according to one embodiment.

A double peaked pressure waveform 300 in the air chamber of an implantable device, such as shown in FIG. 5 may be produced by driving the piston in the compression chamber with a double saw-tooth velocity profile 310, as shown in FIG. 6. As illustrated in FIG. 6, the piston 214 initially moves from its bottom dead center position and toward the top dead center position with an initial linearly decreasing velocity 312. This phase corresponds roughly to the initial increase to the first peak pressure 302 shown in FIG. 5. The piston velocity then increases linearly, corresponding roughly to the phase of the pressure waveform 306 in which the diaphragm moves, the inlet valve closes, the outlet valve opens, and blood is ejected from the device. The piston velocity peaks, and then slows in a linear manner, reaching a second minimum 314 before velocity is again increased linearly toward a second peak 316. The second peak 316 in velocity corresponds to the second pressure peak 304 in the air chamber and may signal complete blood ejection from a blood chamber.

Different types of mechanical and/or electric systems may be used to drive the piston through the compression chamber. According to one embodiment, an electric motor may be connected to the piston through a connecting rod and a Scottish yoke 218 such as shown in FIG. 3. The Scottish yoke converts constant velocity rotation of the electric motor into constant velocity movement of the piston through the compression chamber, at least as the piston moves from top dead center to bottom dead center and vice versa. It is to be appreciated that other types of mechanical and/or electric drive systems may be used to power compressor(s) in a driver, and that the electric motor and Scottish yoke are but one example of such systems.

The systems used to drive compressors may facilitate different types of velocity profiles, and in this respect, may allow drivers to be used for different types of implantable devices. As is to be appreciated, different types of implantable devices replace or assist various functions of a native heart, or other organs, and thus may be associated with different types or pressure and/or flow waveforms for appropriate operation. Embodiments of the driver may produce different pressure waveforms by altering, through controls of the driver, the velocity profile of pistons that move through the compressor and/or pressure settings of pressure relief valves and/or vacuum valves.

Embodiments of the driver may be configured for an extended maintenance interval. According to some embodiments, the seals about the compression chamber(s) include wear resistant materials that do not require lubrication. For example, in some embodiments, the seals between the piston and the cylinder include glass impregnated TEFLON seals and nickel plated interior cylinder walls—a combination of features that has been found to offer an extended maintenance interval. It is to be appreciated that the use of glass impregnated TEFLON seals and nickel plated cylinders is an embodiment of sealing configuration, and that other configurations are also possible.

Figure 7:
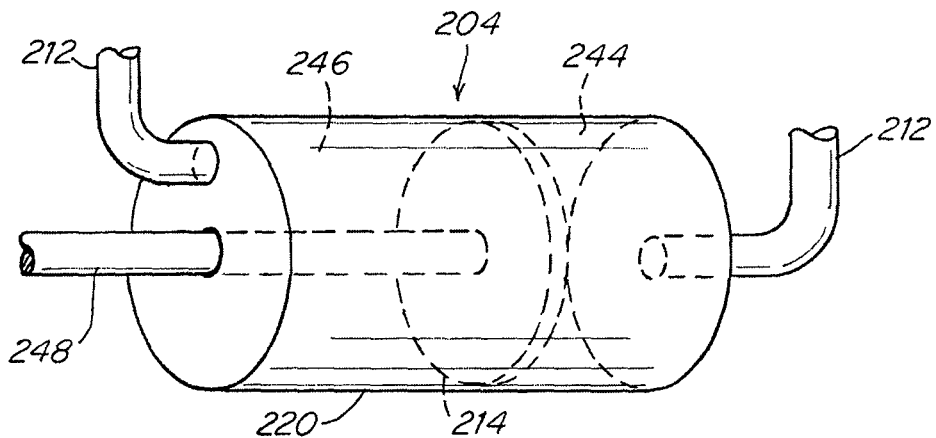
FIG. 7 shows a compressor that includes a first and a second compression chamber, according to one embodiment.

As mentioned herein, a single compressor may incorporate multiple compression chambers such that one compressor may power a left and right ventricle of an artificial heart, if needed. FIG. 7 shows one example of such a compressor 204. The compressor includes a cylinder 220 through which a piston 214 may move. A first compression chamber 244 lies on the top side of the piston and a second compression chamber 246 lies on a bottom side of the piston. A rod 248 that mechanically powers the piston passes through a bottom wall of the second compression chamber. All else constant, the second/bottom compression chamber will have a smaller swept volume than the top chamber because of the presence of the rod in the second/bottom compression chamber. The smaller swept volume of the second/bottom chamber may be suitably matched to drive the right ventricle of an artificial heart, while the first/top chamber may be suitable to drive the left ventricle of an artificial heart, which typically requires higher peak pressures.

Figure 8A:
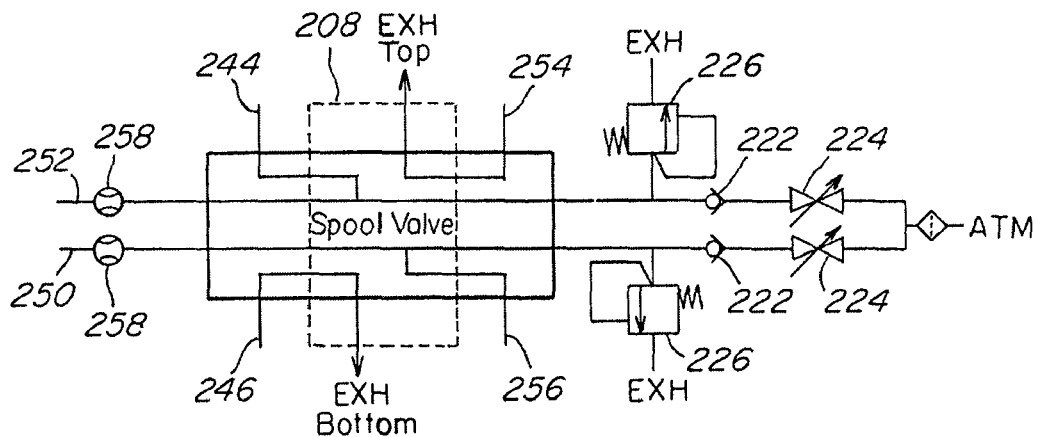
FIGS. 8a-8c are pneumatic diagrams of one embodiment of a driver, in different modes of operation.
Figure 8B:
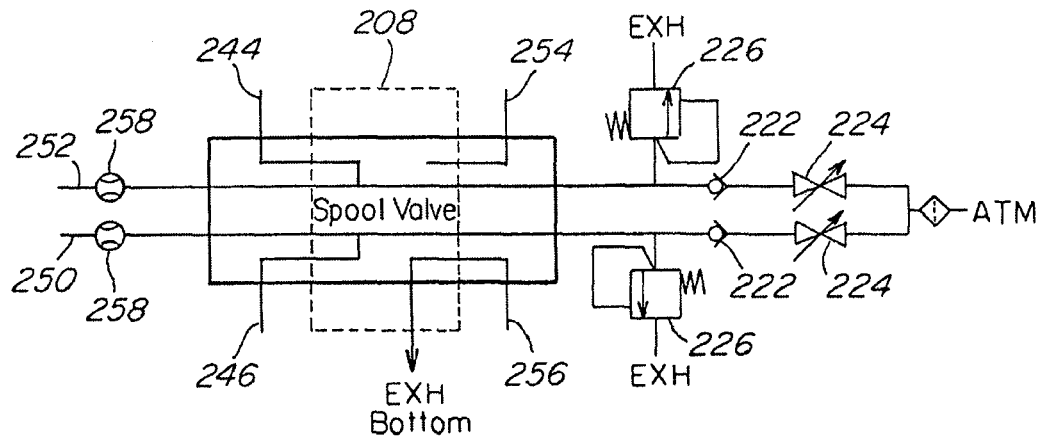
Figure 8C:
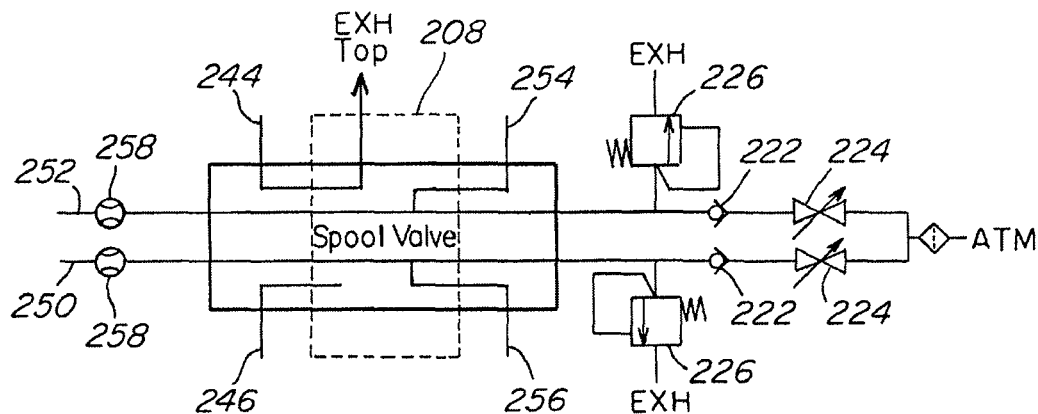

Multiple compressors may be incorporated into a driver to provide redundant support for implantable medical devices. By way of example, the pneumatic diagrams of FIGS. 8a-8c show one embodiment that includes connections to two compressors configured like that shown in FIG. 7 and air outlets 250, 252 for each of the left and right ventricle of an artificial heart. The air outlet 252 for the right ventricle is in fluid communication with a variable vacuum valve 224, a check valve 222, and a pressure relief valve 226. Similarly, the air outlet for the left ventricle 250 is in communication with a variable vacuum valve 224, a check valve 222, and a pressure relief valve 226 which is dedicated for use with the left ventricle of the artificial heart. A spool valve 208 provides selective communication between the air outlet for the right ventricle 252 and two or more of the compression chambers in the driver 200. The same spool valve 208 also provides selective communication between the air outlet 250 for the left ventricle and two or more compression chambers in the driver.

The driver may include features that allow rapid reconfiguration of the fluid connections between air outlets of the driver and compression chambers of the compressors. The spool valve may be moved to any of three different positions as illustrated in FIGS. 8a-8c to provide different fluid connections between the compressors and the driver air outlets for each of the left and right ventricles of an artificial heart, as described below.

FIG. 8a shows the spool valve 208 in a first position that may be associated with a normal mode of operation the driver. Here, the spool valve 208 is positioned to provide fluid communication between a first compression chamber connection 244 and the air outlet 252 associated with the left ventricle of the artificial heart. A fourth compression chamber 256 connection (of the second compressor) is in fluid communication with the air outlet 250 associated with the right ventricle. The second compression chamber connection 246 of the first compressor and the third compression chamber connection 254 of the second compressor are each exhausted to the atmosphere, and are effectively not used during this normal mode of operation.

FIG. 8b shows the spool valve 208 positioned such that the second compressor is no longer in fluid communication with either of the air outlets 250, 252 of the driver, and may be associated with a backup mode of operation of the driver. Here, the first compression chamber connection 244 of the first compressor remains in fluid communication with the air outlet 252 associated with the left ventricle. The second compression chamber connection 246 of the first compressor, however, is in fluid communication with the air outlet 250 associated with the left ventricle, instead of the fourth compression chamber of the second compressor. The spool valve 208 may be moved to the position represented by FIG. 8b when a fault is experienced in the second compressor 206.

If a fault is experienced by the first compressor 204, the spool valve 208 may be moved to provide fluid connections like those shown in FIG. 8c. As shown, the third compression chamber connection 254 and fourth compression chamber connection 256 of the driver 100 (in the second compressor 206) are in fluid communication with the air outlets 252, 250 associated with the left and right ventricles, respectively. The chambers 244, 246 of the first compressor are removed from fluid communication with either of the air outlets.

Embodiments of the driver may switch between modes of operation without causing a reduction in heart rate or blood pressure. Each of the compression chambers that are selectively connectable to the left ventricle air outlet 252 may be sized to support the left ventricle through a full range of operating conditions. Similarly, each of the compression chambers that are selectively connected to the right ventricle air outlet 250 may be sized to support the right ventricle through a full range of operating conditions.

In the first mode described above, each of the left and right ventricles, driven by compression chambers of separate compressors, may be operated synchronously or asynchronously. In synchronous operation, the compression chamber associated with each ventricle is compressed over a common time interval. This causes each of the ventricles to eject blood at roughly the same time. Alternatively, each ventricle may be operated asynchronously, where blood is ejected at different times. As may be appreciated, the mode of operation shown in FIGS. 8b and 8c is asynchronous.

Flow meters 258 may be incorporated into pneumatic systems of the driver. In some embodiments, like those of FIGS. 8a-8c, flow meters are positioned to measure the volume of air that passes through an air outlet, either during systole or diastole of an artificial heart. According to some embodiments, the flow of air is measured as air evacuates the air chamber of the artificial heart and blood fills the blood chamber. This flow information may provide an indication as to how rapidly blood fills the artificial heart, all of which is later ejected from the blood chamber, and in this regard, may be used to calculate blood flow/cardiac output in the subject.

Embodiments of the driver may include features for identifying the type and/or size of implantable device that is connected to the driver. As mentioned herein, the driver may be used with different types of implantable devices, like artificial hearts, ventricular assist devices, and/or intra-aortic balloons. The drivelines associated with such devices may be configured with a feature, such as an RFID tag, that identifies the device to the driver. With the implantable device identified, the driver may be configured with appropriate operating software and/or user interfaces. This configuration may occur automatically, according to some embodiments.

The driver may include features that confirm the type and/or function of an implantable device that is to be driven. In some embodiments, this occurs by cycling the compressors to drive the implantable device through one or more complete compression and/or expansion cycles (prior to the device being implanted in a subject). Measured pressure and/or flow characteristics of the system may then be compared with expected pressure and/or flow characteristics for the implantable device. Conformance between the expected and measured results may be used to confirm the appropriate function of an implantable device.

The driver may include features that facilitate monitoring operation of the driver for faults and automatically switching the driver to backup mode from primary mode upon identifying any of such faults.

According to some embodiments, the position of the first compressor and second compressors, relative to one another, may be monitored for a fault condition. For example, there may be an acceptable range of phases between compression cycles of the first and second compressors when used to power separate ventricles of an artificial heart. In one embodiment, this range is 180 degrees. However, it is to be appreciated that this range may be set to other values based on the desires of a particular user.

The movement of pistons in each compressor may be monitored to identify faults where either of the pistons has stopped moving or has slowed below a threshold value. This may be accomplished, according to some embodiments, by placing one or more position sensors in the compression chamber or somewhere on the mechanism that drives the piston through its range of motion. According to one embodiment, a pair of optical flag sensors is positioned on the motor that drives each compressor. In this embodiment, a fault may be indicated when each of the pair of sensors show that the piston of a corresponding compressor is not operating. Sensors configured redundantly like this may prevent faults from inadvertently being identified when one of the redundant sensors fails but the compressors continue to operate appropriately.

Combinations of pressure and flow through the pneumatic system may also be monitored to identify a fault. For example, when both pressure and flow fall below an expected level of operation, such as 10% below, 15% below, and/or 25% below expected levels, a fault may be indicated. According to some embodiments, normal reduction in pressure and/or flow is accounted for in the monitoring, such as through adaptive control, so to prevent faults from being identified due to normal wear. Monitoring both pressure and flow together, in this manner, may prevent a fault from being indicated inappropriately. For example, in situations where a driveline might be kinked, flow may drop and pressure may increase. Here, a compressor fault would not be identified. Other alarms may be sounded to alert a subject or healthcare professional of the situation, but the driver is not automatically switched to a backup mode, as no fault appears to be associated with the compressors. Similarly, if the drivelines are unplugged from the driver, high flow and low pressure may occur without necessarily indicating a fault that will cause the compressors to operate in backup mode.

Embodiments of the driver may include multiple modes of operation suitable for different settings and/or different users. As is to be appreciated, full access to operating parameters of the driver may be desirable in an operating room setting, where a surgeon may desire to change parameters like heart rate, peak pressure, and flow as the subject's condition may dictate. In this respect, the driver may have an operating room mode that allows full access and control by a user to a wide variety of operating parameters. Changes to these parameters may be made immediately after desired levels are input to the controller.

The driver may also include an intensive care mode, where a user may have limited access to change operating parameters of the driver. Additionally or alternatively, restrictions may be put in place to limit the degree to which operating parameters of the driver may be changed, at least with respect to an operating room mode of the driver. For example, in an intensive care mode, heart rate may be lowered to 90 bpm, while in a corresponding operating mode, heart rate may be lowered further, such as to 40 bpm or even turned of (0 bpm), according to one embodiment.

The driver may request confirmation from a user prior to operating parameters being implemented. For example, when in intensive care mode the driver may prompt the user to enter data two or more times to confirm that data that have been entered. This may be prevent data entry errors from being made by a user and/or ensure that a user has not inadvertently requested a change. According to some embodiments parameter changes may be implemented after a pause, such as after 1 second, 2 second, 5 seconds, or pauses of other lengths of time. According to one embodiment, a user identifies a parameter to be changed by selecting an icon on a screen of the driver. The user is then prompted to enter a new value for the identified parameter. Once the new value is entered, the user is prompted to confirm the change that is about to be made. In some embodiments, this is accomplished by displaying the identified parameter, the prior value of the identified parameter, and the new value for the identified parameter to the user for final confirmation before the change is entered.

Embodiments of the driver may also include a home mode that is suitable for operation when a subject is away from a hospital. In the home mode, access to change parameters may be locked, such that they may not be changed by a user or may only be changed to a limited degree. In this respect, the driver may include safeguards against inadvertent changes to operating parameters.

The ability to change between modes of operation, including an operating room mode, an intensive care mode, and a home mode may require a password. In this respect, controls may be put in place such that changes between modes of operation may be made be qualified individuals and inadvertent changes between modes of operation may be avoided.

Redundant controllers may be incorporated into the driver such that each controller may operate compressors of the driver in the event of fault of the other controller. According to some embodiments, a computer is incorporated into the driver as a first controller. The computer may be a single board computer that includes an operating system, such as QNX, UNIX, or other types of operating systems and may be loaded with software that is capable of operating the driver alone or in combination with other controllers. The computer may additionally or alternately include a second controller configured differently from the first controller. In some embodiments, the second controller is an analog controller that resides on a printed circuit board in the driver. The analog controller may be capable of operating the driver in combination with the first controller, or alone in the event of a fault in the first controller.

Incorporating a computer into the driver may offer functionality that may be desirable by users. For instance, the computer may be capable of monitoring and recording operating parameters of an implantable device, such as pressure waveforms, flow rates and/or cardiac output. Additionally or alternately, parameters associated with the driver, such as electrical power input to compressor motors, torque or force exerted by the motors, battery power levels, and the like, may be monitored and/or recorded. The computer may provide access to such parameters for review by a healthcare professional or technician to help with the care of a subject or maintenance of the driver. According to some embodiments, a graphical user interface, like a touch screen display, is incorporated directly into the driver to provide a user with access to such information.

Redundant power sources may also be incorporated into the driver. In some embodiments, the driver includes rechargeable internal batteries and one or more rechargeable external batteries. The driver may also include an AC/DC converter such that the driver may be powered from a wall socket. The AC/DC converter may also allow internal and/or external batteries of the driver to be recharged, even as the driver is powering an implantable device in operation.

The driver may include a housing 260 for enclosing various devices. The driver in the embodiment of FIG. 9 encloses the pneumatic system 212, excluding the drivelines and implantable device. The housing also encloses the drive mechanisms for the compressors, battery power sources for the compressors, a first controller and a second controller. The first controller comprises an analog controller and the second controller that comprises an integrated single board computer that includes a touch screen user interface, a motherboard, a video card, an audio chip, a ram, a processor, a touchscreen display and connection points for expansion boards and connections for other devices, such as USB and RJ-45 type connections, among other features.

Figure 9:
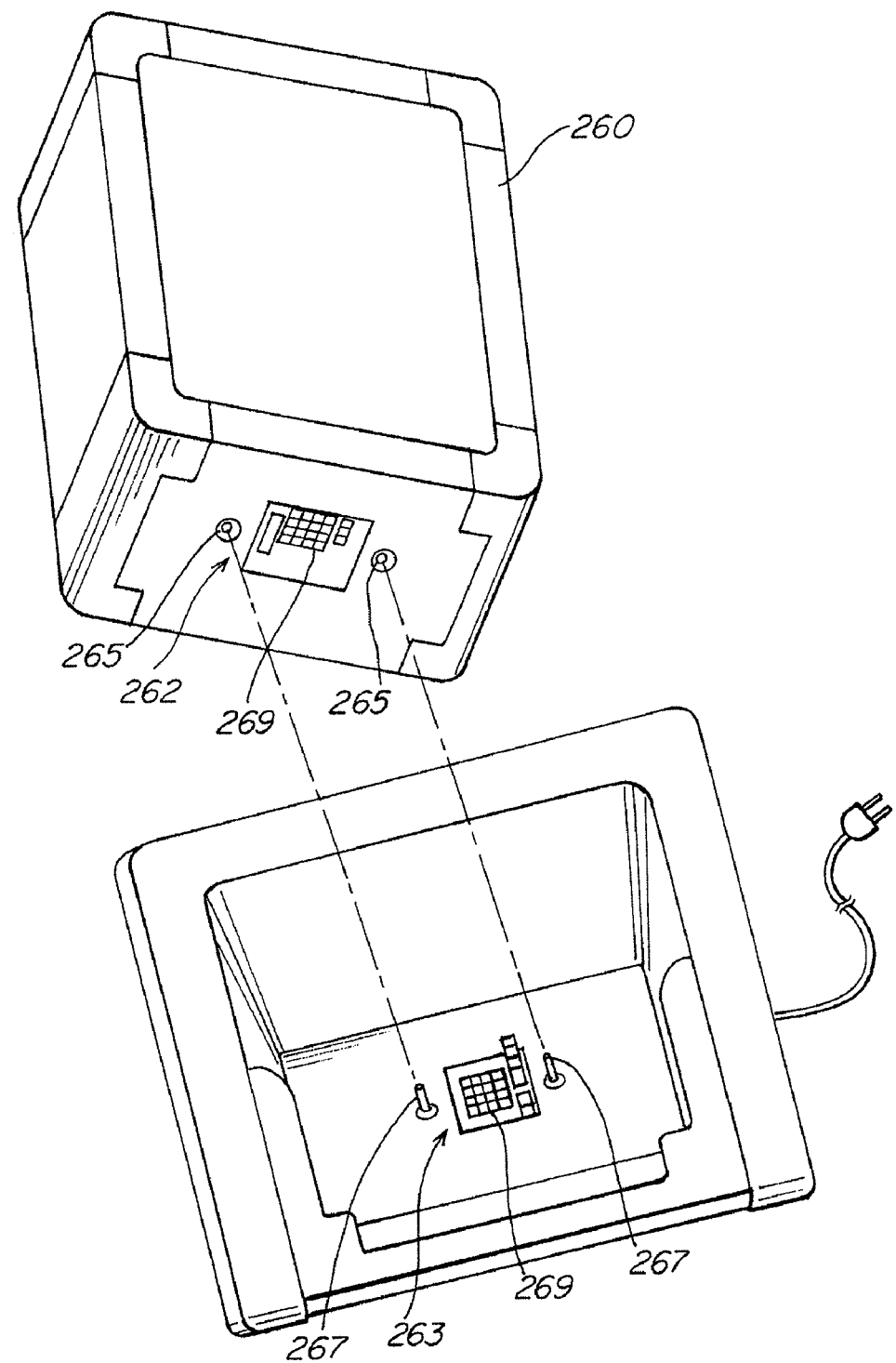
FIG. 9 shows a driver and a dock that receives the driver, according to one embodiment.

The driver housing may include a dockable interface 262 to facilitate connections to host devices, such as a corresponding dockable interface 263 that may be incorporated into a hospital cart 320 or personal caddy 322 for the driver. As shown in FIG. 9, one embodiment of the driver includes a face with receptacles 265 that receive guide pins 267 of a mating dock. The driver, once aligned with the guide pins, may be slid toward a docked position, where the full weight of the driver is supported. The dock may include features which mechanically lock the housing in place on the dock once received. Multiple electrical connections, including power and data connections 269, may be engaged as the driver is slid to the docked position. In some embodiments, components of the host device may automatically turn on when the driver is received. Additionally, redundant connections for data and/or power may be included within the dockable interface.

Figure 10:
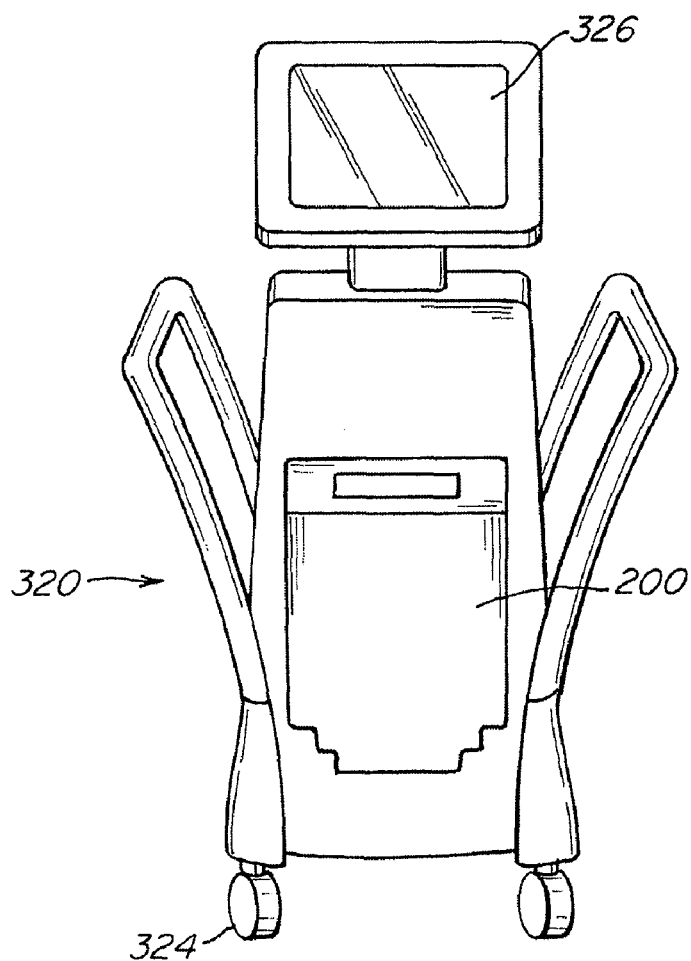
FIG. 10 shows a cart that may dock with the driver, according to one embodiment.
Figure 11:
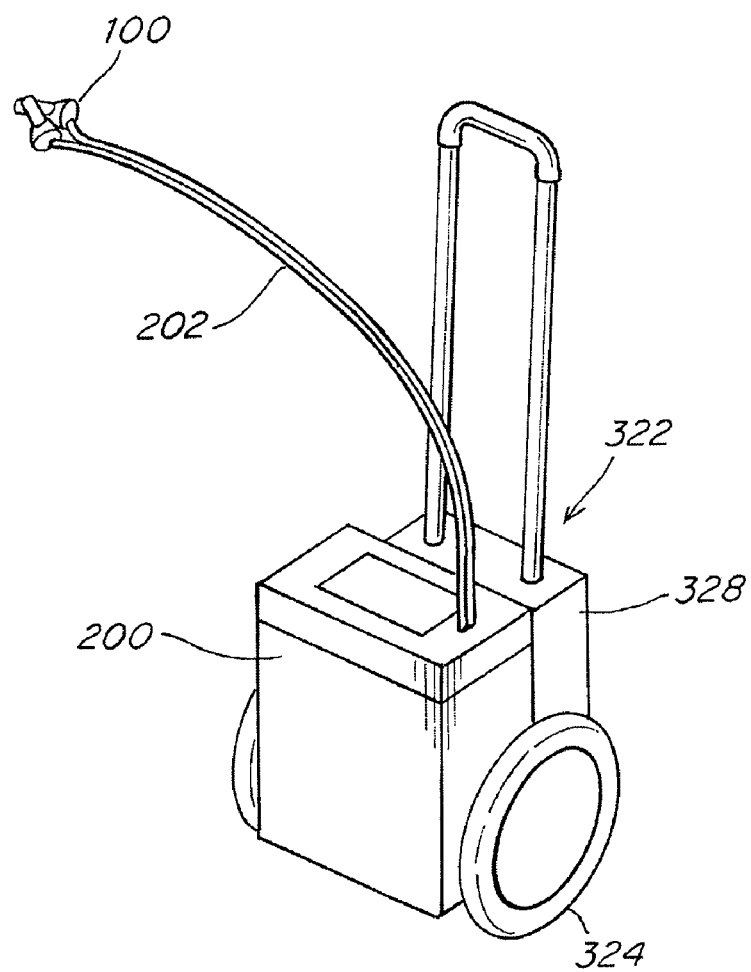
FIG. 11 shows a caddy that may dock with the driver, according to one embodiment.

In one illustrative embodiment, the host device for the driver may include a cart 320 that is configured for use in the hospital setting, like that shown in FIG. 10. The hospital cart 320 includes wheels or casters 324 suitable for moving the cart about a hospital. The cart also includes an integrated power supply 328 to provide power to the driver, either from rechargeable batteries or a wall socket, and to recharge batteries of the driver. The user interface of the cart may include a touch-sensitive display screen 326, and may be automatically turned on when the driver is received by the cart. Another illustrative embodiment of the host device may include a caddy 322, as shown in FIG. 11, which includes a dock connection, a pair of tires, a telescoping handle, and an integrated power supply.

Having thus described several aspects of at least one embodiment of this invention, it is to be appreciated various alterations, modifications, and improvements will readily occur to those skilled in the art. Such alterations, modification, and improvements are intended to be part of this disclosure, and are intended to be within the spirit and scope of the invention. Accordingly, the description and drawings herein are by way of example only.

The invention claimed is:

1. A pulsatile pneumatic driver configured to provide pneumatic power to an implantable artificial heart, the driver comprising:
   a first compressor that includes a first pair of compression chambers, at least one of the first pair of compression chambers having a swept volume that is at least 160 cubic centimeters;
   a second compressor that includes a second pair of compression chambers, at least one of the second pair of compression chambers having a swept volume that is at least 160 cubic centimeters;
   a first air outlet and a second air outlet in selective communication with two or more compression chambers of the first and second pair of compression chambers; and
   a valve that is movable between a normal operation position associated with a normal mode of operation of the driver, a first backup position associated with a first backup mode of operation of the driver and a second backup position associated with a second backup mode of operation of the driver;
   wherein when in the normal mode of operation, the first air outlet is in fluid communication with one of the first pair of compression chambers and the second air outlet is in fluid communication with one of the second pair of compression chambers;
   wherein when in the first backup mode of operation, the first air outlet is in fluid communication with one of the first pair of compression chambers and the second air outlet is in fluid communication with another of the first pair of compression chambers; and
   wherein when in the second backup mode of operation, the first air outlet is in fluid communication with one of the second pair of compression chambers and the second air outlet is in fluid communication with another of the second pair of compression chambers.

2. The pulsatile pneumatic driver of claim 1, further comprising:
   a controller;
   a first pressure sensor in fluid communication with the first air outlet and a second pressure sensor in fluid communication with the second air outlet;
   a first pressure relief valve in fluid communication with the first air outlet and a second pressure relief valve in fluid communication with the second air outlet;
   wherein the controller controls each of the first and second pressure relief valves to open at a pressure, as sensed by the first and second pressure sensors, respectively.

3. The pulsatile pneumatic driver of claim 1, further comprising:
   a controller;
   a first pressure sensor in fluid communication with the first air outlet and a second pressure sensor in fluid communication with the second air outlet;
   a first vacuum valve in fluid communication with the first air outlet and a second vacuum valve in fluid communication with the second air outlet, wherein the controller controls each of the first and second vacuum valves to maintain a user-defined vacuum level at the first and second air outlet, respectively, as a corresponding compression chamber is expanded.

4. The pulsatile pneumatic driver of claim 3, wherein each of the first and second vacuum valves comprise a gate valve having a gate with a tear-drop shaped aperture.

5. The pulsatile pneumatic driver of claim 4, further comprising:
- a first check valve positioned between the first air outlet and the first vacuum valve, the first check valve configured to close fluid communication between the first air outlet and the first vacuum valve during compression of a corresponding compressor; and
- a second check valve positioned between the second air outlet and the second vacuum valve, the second check valve configured to close fluid communication between the second air outlet and the second vacuum valve during compression of a corresponding compressor.

6. The pulsatile pneumatic driver of claim 1, wherein each of the first pair of compression chambers and each of the second pair of compression chambers has a swept volume that is at least 195 cubic centimeters.

7. The pulsatile pneumatic driver of claim 1, further comprising:
- an implantable artificial heart having a right ventricle in fluid communication with the first air outlet and a left ventricle in fluid communication with the second air outlet.

8. The pulsatile pneumatic driver of claim 7, wherein each of the left and right ventricles has a displacement of 70 cubic centimeters.

9. The pulsatile pneumatic driver of claim 7, wherein at least one of the first pair of compressors and at least one of the second pair of compressors has a swept volume that is more than 2.5 times the displacement of each of the left and right ventricles of the implantable artificial heart.

10. The pulsatile pneumatic driver of claim 1, wherein the first compressor includes a first cylinder and a first piston that moves through the cylinder, wherein one of the first pair of compression chambers lies on a first side of the first piston and another of the first pair of compression chambers lies on a second side of the first piston; and
- wherein the second compressor includes a second cylinder and a second piston that moves through the second cylinder, wherein one of the second pair of compression chambers lies on a first side of the piston and another of the second pair of compression chambers lies on a second side of the second piston.

11. The pulsatile pneumatic driver of claim 10, further comprising:
- a first seal between the first cylinder and the first piston and a second seal between the second cylinder and the second piston, each of the first and second seals being free of liquid lubrication.

12. A pulsatile pneumatic driver configured to provide pneumatic power to an implantable artificial heart, the driver comprising:
- a first compressor that includes a first pair of compression chambers;
- a second compressor that includes a second pair of compression chambers;
- a first air outlet and a second air outlet in selective communication with two or more compression chambers of the first and second pair of compression chambers;
- a valve that is movable between a normal operation position associated with a normal mode of operation of the driver, a first backup position associated with a first backup mode of operation of the driver and a second backup position associated with a second backup mode of operation of the driver;
- wherein when in the normal mode of operation, the first air outlet is in fluid communication with one of the first pair of compression chambers and the second air outlet is in fluid communication with one of the second pair of compression chambers;
- wherein when in the first backup mode of operation, the first air outlet is in fluid communication with one of the first pair of compression chambers and the second air outlet is in fluid communication with another of the first pair of compression chambers; and
- wherein when in the second backup mode of operation, the first air outlet is in fluid communication with one of the second pair of compression chambers and the second air outlet is in fluid communication with another of the second pair of compression chambers;
- a controller that monitors operation of the driver and causes the valve to move from the normal operation position to one of the first and second backup positions upon detection of a fault;
- wherein the fault comprises the first and second compressors operating more than 180 degrees out of phase with one another.

13. A pulsatile pneumatic driver configured to provide pneumatic power to an implantable artificial heart, the driver comprising:
- a first compressor that includes a first pair of compression chambers;
- a second compressor that includes a second pair of compression chambers;
- a first air outlet and a second air outlet in selective communication with two or more compression chambers of the first and second pair of compression chambers;
- a valve that is movable between a normal operation position associated with a normal mode of operation of the driver, a first backup position associated with a first backup mode of operation of the driver and a second backup position associated with a second backup mode of operation of the driver;
- wherein when in the normal mode of operation, the first air outlet is in fluid communication with one of the first pair of compression chambers and the second air outlet is in fluid communication with one of the second pair of compression chambers;
- wherein when in the first backup mode of operation, the first air outlet is in fluid communication with one of the first pair of compression chambers and the second air outlet is in fluid communication with another of the first pair of compression chambers; and
- wherein when in the second backup mode of operation, the first air outlet is in fluid communication with one of the second pair of compression chambers and the second air outlet is in fluid communication with another of the second pair of compression chambers;
- a controller that monitors operation of the driver and causes the valve to move from the normal operation position to one of the first and second backup positions upon detection of a fault;
- wherein the controller monitors a first pair of redundant position sensors associated with the first compressor and a second pair of redundant position sensors associated with the second compressor to determine the fault.

14. A pulsatile pneumatic driver configured to provide pneumatic power to an implantable artificial heart, the driver comprising:
- a first compressor that includes a first pair of compression chambers;
- a second compressor that includes a second pair of compression chambers;

a first air outlet and a second air outlet in selective communication with two or more compression chambers of the first and second pair of compression chambers;

a valve that is movable between a normal operation position associated with a normal mode of operation of the driver, a first backup position associated with a first backup mode of operation of the driver and a second backup position associated with a second backup mode of operation of the driver;

wherein when in the normal mode of operation, the first air outlet is in fluid communication with one of the first pair of compression chambers and the second air outlet is in fluid communication with one of the second pair of compression chambers;

wherein when in the first backup mode of operation, the first air outlet is in fluid communication with one of the first pair of compression chambers and the second air outlet is in fluid communication with another of the first pair of compression chambers; and wherein when in the second backup mode of operation, the first air outlet is in fluid communication with one of the second pair of compression chambers and the second air outlet is in fluid communication with another of the second pair of compression chambers;

a controller that monitors operation of the driver and causes the valve to move from the normal operation position to one of the first and second backup positions upon detection of a fault;

wherein the controller monitors pressure and flow rate associated with each of the first and second air outlets to identify the fault.

* * * * *